(12) United States Patent
Kralovec et al.

(10) Patent No.: US 7,504,115 B2
(45) Date of Patent: Mar. 17, 2009

(54) SHARK CARTILAGE EXTRACTS AND USE THEREOF FOR IMMUNOMODULATION

(75) Inventors: Jaroslav A. Kralovec, Halifax (CA); Frank Chung-Yin Sing, Halifax (CA)

(73) Assignee: Ocean Nutrition Canada Limited, Halifax Nova Scotia (CA)

(*) Notice: Subject to any disclaimer, the term of this patent is extended or adjusted under 35 U.S.C. 154(b) by 35 days.

(21) Appl. No.: 10/503,518

(22) PCT Filed: Feb. 15, 2002

(86) PCT No.: PCT/CA02/00174

§ 371 (c)(1), (2), (4) Date: Mar. 17, 2005

(87) PCT Pub. No.: WO03/068249

PCT Pub. Date: Aug. 21, 2003

(65) Prior Publication Data

US 2005/0175711 A1 Aug. 11, 2005

(51) Int. Cl.
*A61K 35/34* (2006.01)
*A61K 38/00* (2006.01)
*A61K 38/17* (2006.01)

(52) U.S. Cl. .......................... 424/548; 514/21; 530/353
(58) Field of Classification Search ................ 424/548; 514/21; 530/353
See application file for complete search history.

(56) References Cited

U.S. PATENT DOCUMENTS

| 4,473,551 | A | * | 9/1984 | Schinitsky | .................. 424/548 |
| 5,075,112 | A | | 12/1991 | Lane | |
| 5,618,925 | A | | 4/1997 | Dupont et al. | |
| 5,840,342 | A | | 11/1998 | Raithaus | |
| 6,028,118 | A | * | 2/2000 | Dupont et al. | .............. 424/548 |
| 6,096,346 | A | | 8/2000 | Chen | |
| 6,168,807 | B1 | * | 1/2001 | Dupont et al. | .............. 424/548 |
| 6,255,295 | B1 | * | 7/2001 | Henderson et al. | ............ 514/54 |
| 6,380,366 | B1 | * | 4/2002 | Dupont et al. | .............. 530/422 |

FOREIGN PATENT DOCUMENTS

| CA | 2201025 | 9/1998 |
| WO | WO 97/16197 | 5/1997 |
| WO | WO 00/04910 | 2/2000 |

OTHER PUBLICATIONS

Chondroitin sulfate. http://www.pdrhealth.com/drug_info/nmdrugprofiles/nutsupdrugs/cho_0071.shtml p. 1-6.*
Fontenele et al., 1997. The Analgesic and anti-inflammatory Effects of Shark Cartilage Are Due to a Peptide Molecule and Are Nitric Oxide (NO) System Dependent. Biol. Pharm. Bull., vol. 20 (1 I), pp. 1151-1154.*
Chondroitin sulfate. 2003. http://web.archive.org/web/20030812170220/http://www.pdrhealth.com/drug_info/nmdrugprofiles/nutsupdrugs/cho_0071.shtml.*
Meningitis-Causes. 2008. http://www.mayoclinic.com/health/meningitis/DS00118/DSECTION=3. p. 1-3.*
Meningitis-Treatment. 2008. http://www.mayoclinic.com/health/meningitis/DS00118/DSECTION=8. p. 1-2.*
Abstract: XP-002219069; Geise, S. et al.; "Influence of the oral ingestion of shark cartilage and rice bran on the immune system in a rat model," *Society of Neuroscience Abstracts*, vol. 27 (1) p. 22, 2001; Accession No. PREV200100483327.
Sivakumar, P. et al.; "Occurrence of a novel collagen with three distinct chains in the cranial cartilage of the squid *Sepia officinalis*: comparison with shark cartilage collagen," *Biochimica et Biophysica Acta*, vol. 1381 (1998) pp. 161-169.
Sculti, Leon; "Arthritis Benefits from Shark Cartilage Therapy," *Alternative and Complementary Therapies*, pp. 35-37, (Oct. 1997).
Fontenele, Juvenia Bezerra et al.; "The Analgesic and Anti-inflammatory Effects of Shark Cartilage Are Due to a Peptide Molecule and Are Nitric Oxide (NO) System Dependent," *Biol. Pharm. Bull.*, vol. 20 (11), pp. 1151-1154, (1997).
Fontenele, J.B. et al.; "Anti-inflammatory and analgesic activity of a water-soluble fraction from shark cartilage," *Brazilian Journal of Medical and Biological Research*, vol. 29 (5), pp. 643-646, (1996).
Rosen, J. et al.; "Immunoregulatory Effects of Catrix," *Journal of Biological Response Modifiers*, vol. 7 (5), pp. 498-512, (1988).
Kasai, Noriyuki et al.; "Delayed-Type Hypersensitivity Induced by Bovine Nasal Cartilage Protoeoglycan in Guinea Pigs," *Connective Tissue Research*, vol. 14, pp. 221-228, (1986).
Kralovec, J.A., et al.; "Immunomodulating principles from shark cartilage Part 1. Isolation and biological assessment in vitro," *International Immunopharmacology*, vol. 3, pp. 657-669, (2003).

* cited by examiner

*Primary Examiner*—L Blaine Lankford
*Assistant Examiner*—Taeyoon Kim
(74) *Attorney, Agent, or Firm*—Husch Blackwell Sanders LLP Welsh & Katz

(57) ABSTRACT

Disclosed is a composition from shark cartilage comprising immunoactive proteoglycans and other immunoactive components having a molecular weight greater than about 100 KD, wherein the composition has a uronic acid content of about 0.05-0.5 μg glucuronic acid per μg of the composition. The composition may be useful for treating or preventing tumor growth, bacterial infections, viral infections and/or fungal infections.

12 Claims, 5 Drawing Sheets

SHARK CARTILAGE EXTRACTS AND USE THEREOF FOR IMMUNOMODULATION

FIELD OF THE INVENTION

The present invention relates to compositions comprising active principles from shark cartilage, methods of producing such compositions and use of such compositions as immunomodulators.

BACKGROUND OF THE INVENTION

Shark cartilage has traditionally been credited with a number of medical benefits but it is primarily marketed for its anticancer effects [1-5]. The potential value of shark cartilage in cancer treatment as an angiogenesis inhibitor [6-8] has been investigated and several clinical trials have been done or are underway. However, its efficacy has been controversial thus far [9-14].

In addition, there have been a number of other bioactivities attributed to shark cartilage, including beneficial effects on osteoarthritis, rheumatoid arthritis, progressive systemic sclerosis and neurovascular glaucoma, just to name a few [15-17]. There are suggestions that shark cartilage also contains anti-inflammatory agents and wound healing substances [15, 18, 19]. There has been speculation, rather than scientific evidence, that shark cartilage may stimulate the cellular and humoral components of the immune system, presumably making it effective against tumor growth and bacterial, viral and fungal infections. Several shark cartilage preparations claiming immune-boosting effects are on the market (Cartilade™ from Cartilage Technologies Inc.; SC Formula, from Nature's Sunshine, etc). An extract of shark liver has recently been found to stimulate the immune system [20] and Rosen et al [21] reported on immunoregulatory effects of a bovine cartilage preparation (CatrixS™). They disclose that fractions with 0-10 KD and 30-100 KD range enhanced T-dependent and T-independent antibody responses in vivo, possibly related to the chondroitin sulfate component.

A variety of shark cartilage products have been introduced as dietary supplements or even tested in clinical practice, however, many of the claims of purity, bioactivity and clinical efficacy are not backed by rigorous scientific investigation. Although there has been progress in the understanding of the field, the isolation, purification, analysis and standardization of these materials are still extremely challenging.

There has been controversy as to whether shark cartilage could be effective via oral administration. The active principles of shark cartilage described in the literature and believed to be behind various activities are biopolymers, usually proteins. Pettit and Ode isolated two glycoproteins from shark cartilage: sphyrnastatin 1 and 2 [22]. McGuire et al demonstrated antiproliferative activity of a heat stable, <10 KD fraction of shark cartilage extract on endothelial cell population [4]. This is in agreement with Oikawa's work, where a substance with an average molecular mass of 1-10 KD was isolated from shark cartilage. Oikawa's material was heat stable, however no information on the composition of the substance was given and the material was not administered orally [23]. Suzuki et al isolated from shark cartilage a fraction of large molecular mass inhibiting solid tumor growth [24]. Another preparation, a patented anti-inflammatory substance isolated from shark cartilage, was of molecular mass larger than 100 KD [25], however this substance was not intended for oral administration.

Proteins have low oral bioavailability and short in vivo half-lives, which to date have necessitated their delivery by infusion or frequent injections [26]. In the case of antigen delivery, biodegradable and biocompatible microspheres have been used for antigen delivery into the GI tract [27]. Conventional wisdom says that biopolymers would be either disintegrated into monomers, or smaller or larger oligomers, and thus lose biological activity, (a classical problem with protein or peptide based pharmaceuticals), or if they remained unchanged or were cleaved into large non-absorbable fragments, they would be incapable of exerting their biological effect due to physical barrier.

Except for the reports from questionable clinical trials and other anecdotal evidence [28, 29, 30] there are only a limited number of published scientific papers demonstrating biological effects due to oral administration of shark cartilage preparations. As an example, one study demonstrated a positive effect of shark cartilage on the survival time of rats with implanted intracranial tumor [31].

The protein and carbohydrate components of shark cartilage extracts come largely from proteoglycans (PG) and represent up to 50% of its dry weight [32]. Cartilage also contains collagen and glycosaminoglycans (GAGs), including chondroitins A, B, and C. The GAG part of PG is known to inhibit proliferation of fibroblasts. A number of GAGs, such as heparin and heparan sulfate, have been shown to interact with a wide range of growth factors and cytokines, including α-FGF, β-FGF, GM-GSF, IL-1a, IL1b, IL-2, IL-3, IL-4, IL-6, IL-7, IL-8, hIL-10, vIL-10 and INF-γ. This interaction has been shown to be important in modulating the activity of these growth factors. Shark cartilage contains PGs, GAGs (e.g. CHS A, 1 and C) and collagen. PGs stimulate the immune system, which works synergistically with protein to fight disease [33].

Proteoglycans might be involved in the interaction of primitive, hematopoietic progenitor cells and stromal cells. IL-3 and GM-GSF can be bound by heparan sulfate. PGs form bone-marrow stromal cells or their extracellular matrix and can be presented in a biologically active form of hematopoietic cells. Proteoglycans might also be involved in cell adhesion and homing of hematopoietic stem and progenitor cells [34].

SUMMARY OF THE INVENTION

There is provided a composition from shark cartilage comprising proteoglycans and an immunoactive component having a molecular weight greater than about 100 KD, wherein the composition has a uronic acid content of about 0.05-0.5 μg glucuronic acid per μg of the composition.

There is further provided a formulation comprising an immunomodulating effective amount of a composition from shark cartilage containing proteoglycan and an immunoactive component having a molecular weight greater than about 100 KD, together with a physiologically acceptable carrier, excipient and/or diluent, wherein the composition has a uronic acid content of about 0.05-0.5 μg glucuronic acid per μg of the composition.

There is yet further provided a use of an immunomodulating effective amount of a composition from shark cartilage containing proteoglycans and an immunoactive component having a molecular weight greater than about 100 KD, wherein the composition has a uronic acid content of about 0.05-0.5 μg glucuronic acid per μg of the composition, for modulating an immune system of a subject in need of immunomodulation.

Still further, there is provided a method comprising administering to a subject in need of immunomodulation an immunomodulating effective amount of a composition from shark cartilage containing proteoglycan and an immunoactive component having a molecular weight greater than about 100 KD, wherein the composition has a uronic acid content of about 0.05-0.5 µg glucuronic acid per µg of the composition.

Still yet further, there is provided a commercial package comprising an immunomodulating effective amount of a composition from shark cartilage containing proteoglycan and an immunoactive component having a molecular weight greater than about 100 KD, wherein the composition has a uronic acid content of about 0.05-0.5 µg glucuronic acid per µg of the composition, together with instructions for its use in modulating an immune system of a subject in need of immunomodulation.

DETAILED DESCRIPTION

| Abbreviations: | |
|---|---|
| α-FGF | acidic fibroblast growth factor |
| APMSF | 4-amidinophenylmethanesulfonyl fluoride HCl |
| β-FGF | basic fibroblast growth factor |
| BCA | bicinchoninic acid |
| BSA | bovine serum albumin |
| CHS | Chondroitin sulfate |
| DMAB | p-dimethylamino benzaldehyde |
| DMB | 1,9-dimethyl-methylene blue |
| ELISA | enzyme linked immunosorbent assay |
| GAG | glycosaminoglycan |
| GM-CSF | granulocyte-macrophage colony stimulating factor |
| GuCl | Guanidine hydrochloride |
| IL | interleukin |
| INF-γ | interferon gamma |
| KD | kilodalton |
| LPS | lipopolysaccharide |
| mAb | Monoclonal antibody |
| MD | megadalton |
| mw | Molecular weight |
| MWCO | molecular weight cut-off |
| MOPS | 3-(N-morpholino)-propane sulfonic acid |
| Na$_2$EDTA | ethylene tetraacetic acid disodium salt |
| NK | natural killer |
| PG | proteoglycan |
| PBS | phosphate buffered saline |
| PMSF | Phenylmethanesulfonyl fluoride |
| PP | Peyer's patches |
| SEC | Size exclusion chromatography |
| TBS | tris buffered saline |
| TMB | tetramethyl benzidine substrate |
| TPCK | N-tosyl-L-phenylalanine chloromethyl ketone |

Compositions:

Shark cartilage compositions of the present invention comprise an immunoactive component having a molecular weight greater than about 100 KD. The average molecular weight is about 500 KD. In particular, components having a molecular weight greater than about 500 KD, even more particularly greater than about 1 MD, are implicated in the immunoactivity exhibited by the compositions.

One category of components that make up the shark cartilage immune boosting preaparation are proteoglycans. Proteoglycans are a class of glycosylated proteins, which have covalently linked sulfated glycosaminoglycans, (i.e., chondroitin sulfate, dermatan sulfate, heparan sulfate, heparin, keratan sulfate). Glycosaminoglycans are sulfated polysaccharides made of repeating disaccharides (typically a repeat of 40-100 times), which consist of uronic acid (or galactose) and hexosamines. Components of the disaccharides are (glucuronic acid/iduronic acid —N-acetylgalactosamine) in chondroitin sulfate and dermatan sulfate, (glucuronic acid/iduronic acid —N-acetylglucosamine) in heparan sulfate and heparin, and (galactose —N-acetylglucosamine) in keratan sulfate.

Uronic acid is a component of proteoglycans. In shark cartilage compositions of the present invention, the uronic acid content is preferably from about 0.05 to about 0.5 µg glucuronic acid per µg of the composition, more particularly from about 0.08 to about 0.3 µg/µg.

Proteoglycan content of shark cartilage compositions of the present invention may be measured as the index of proteoglycan content, which is defined as the ratio of the composition's proteoglycan content to the proteoglycan content of the supernatant of 40% ammonium sulfate precipitation. The index of proteoglycan content is preferably from about 0.1 to about 1.0, more particularly from about 0.3 to about 0.8.

While it is believed that the immunoactive components of the composition are proteoglycans, the immunoactive components may be different from proteoglycans or may be a combination of proteoglycans and other component of the composition.

The composition may contain xylose, rhamnose, galactose, glucose or mixtures thereof.

Proteins are present in the composition in an amount of about 20-30% by weight of the composition, particularly about 25% by weight. All major amino acids were present. Based on a weight percentage of total amino acid content, glycine content may be from about 14-16%, proline content may be from about 14-15%, alanine content may be from about 12-14%, glutamic acid content may be from about 10-12%, aspartic acid content may be from about 6-7% and arginine content may be from about 5-7%. The predominance of glycine and proline suggests the presence of significant amounts of collagen in the compositions.

Methods of Preparation:

Shark cartilage compositions of the present invention are typically prepared from shark cartilage by extraction methods. Generally, compositions are prepared by extracting the active immunomodulating principles from shark cartilage into an extraction medium, separating unwanted solid materials from the extract, and lyophilizing or freeze-drying the extract to yield solid shark cartilage composition.

There are a number of additional steps that may be performed in a variety of combinations in connection with the generalized method. The shark cartilage may be initially ground or pulverized to increase efficiency of extraction. Unwanted solids may be washed and the washings further combined with the extract to increase yield of the active immunomodulating principles. The extract may be reduced in volume before lyophilization or freeze-drying. The extract may be dialyzed and/or fractionated by ultrafiltration before lyophilization or freeze-drying. The active immunomodulating principles may be precipitated from the extracts and redissolved in another medium before lyophilization. Chromatography may be performed on the lyophilized composition.

Grinding or pulverizing shark cartilage may be performed by any suitable method known in the art. For small samples, a mortar and pestle is appropriate. For large samples, grinding mills or industrial scale pulverizers are more useful. The extent of grinding or pulverizing is not important.

A variety of extraction media may be used. Aqueous media, with or without additional extraction aids, are preferred. Extraction may be typically performed at temperatures from about 0° C.-100° C. Temperatures in excess of 100° C. may be used, but extractions at these temperatures are typically done under pressure.

When water is used alone, it is preferred to perform the extraction at an elevated temperature, typically at a temperature of from about 55° C.-95° C., more preferably from about 75° C.-90° C. Extractions into hot water are typically done for about 0.5-3 hours, more particularly for about 1-2 hours. When lower temperatures (ambient, 4° C., etc.) and longer times are used for the extraction, preservatives, such as $NaN_3$, can be used to prevent bacterial growth.

A number of chaotropic agents may be added to the extraction medium to facilitate extraction. Monovalent salts such as halides with monovalent or divalent cations (e.g. LiCl, $CaCl_2$, $MgCl_2$, $LaCl_2$) and guanidine (e.g. guanidine hydrochloride (GuCl)) are preferred, with GuCl being a particularly preferred chaotropic agent. The chaotropic agent is preferably used in an amount of up to the saturation point, preferably from about 2-6 M. Extractions with aqueous media comprising chaotropic agents are typically done at lower temperatures but for longer times than extractions with pure water. Typically the extraction temperature is from about 0° C.-25° C., more particularly from about 2° C.-10° C. Extraction time is typically on the order of about 12-96 hours, more particularly from about 24-72 hours.

Other additives may be present in the extraction medium. The extraction medium may be buffered using any number of a great variety of buffers known in the art (citrate, tris, MES, ADA, PIPES, MOPS, etc.). A preferred buffer is MOPS, providing a buffered pH of about 6.5. Complexing agents (such as EDTA, citrate, hydroxypyridones, etc.), protease inhibitors (such as benzamidine, 1,10-phenanthroline, TPCK, PMSF, APMSF, etc.), and other additives may also be used.

Typically about 2-50 volumes, particularly about 2-5 volumes of the extraction medium is used for the extraction of the active immunomodulating principles. In addition, the extraction is typically performed under gentle agitation, which may be achieved by agitating the extraction vessel, by mechanically stirring the slurry or through the action of heating the slurry.

Once the extraction period is complete, the extract containing the active immunomodulating principles is typically separated from any unwanted solid material. Separation may be accomplished by any method known in the art, such as centrifugation or filtration. Cross-flow filtration and vibrating membrane filtration followed by microfiltration are preferred methods of filtration. However, centrifugation is preferred over filtration, although microfiltration can be used in conjunction with centrifugation. Centrifugation at 150-25,000 g for a time of about 15-60 minutes is generally satisfactory. One skilled in the art will understand that centrifuge speed and time are related and will be able to adjust speed and/or time accordingly to achieve the desired separation.

The extract may be used in subsequent steps or the unwanted solids may be washed and the washings combined with the extract. Washing may be done with adequately preserved water or with fresh extract and may be done any number of times. The extract, with or without added washings, may be reduced in volume by evaporation if desired.

The extract may be subject to direct lyophilization or freeze-drying to obtain a shark cartilage composition comprising the active immunomodulating principles. Lyophilization or preferably spray-drying are used in the drying step.

The extract may be subjected to other purification steps before or after lyophilization or freeze-drying. Dialysis is typically performed before the lyophilization/freeze-drying step. Dialysis may be done against any number of different aqueous media including, but not limited to, diluted alcohols, various buffers (e.g. Tris buffer), diluted acetic acid and pure water, and may be performed against a membrane having a desired molecular weight cut off. Instead of or in addition to dialysis, the extract may be ultrafiltered through membranes by methods generally known in the art. A single ultrafiltration membrane or a series of membranes having increasing molecular weight cut-offs may be used. The molecular weight cut-off for such membranes is typically in the range of about 10-3000 KD, for example, 30 KD, 100 KD, 500 KD and 1000 KD. Dialysis could also be replaced by desalting with gel filtration media such as Sephadex™ G-25, Bio Gel™ P-6 or equivalents.

The active immunomodulating principles may be precipitated from the separated extract using a precipitant, such as ethanol or ammonium sulfate, instead of or in addition to the other purification steps. A final ethanol concentration of about 70-90% by volume, more preferably about 80%, is typical, while a final concentration of about 15-45% w/v, preferably 40%, is typical for ammonium sulfate. Such precipitation is typically carried out over a period of 12-24 hours in a refrigerator (e.g. about 2-10° C.). The precipitated immunomodulating principle may then be redissolved in water or buffer and subsequent purification performed.

Subsequent to lyophilization, further purification may be accomplished by way of chromatography or ultrafiltration. Chromatographic fractionation may be achieved using size exclusion or ion exchange matrices such as Sephadex™, Sephacryl™ or DEAE Sepharose™ media. One skilled in the art will understand how to choose appropriate fractionation ranges, for example, Sephadex™ G-100 may be used for a molecular weight cut off of about 100 KD. Sephadex™ G-100, Sephacryl™ S-300 HR and DEAE Sepharose™ are preferred examples of chromatographic media. One skilled in the art will be able to choose appropriate eluants depending on the chromatographic matrix used and the desired fractionation. Such eluents are well known in the art and include, for example, buffers (such as acetate, phosphate and Tris buffers) and aqueous sodium formate. Acetate buffer is particularly preferred for DEAE Sepharose™ while aqueous sodium formate is particularly preferred for Sephadex™ and Sephacryl™. Other additives may be used to alter the solubility conditions and may be optimized for the particular chromatographic matrix and/or eluant. For example, sodium chloride and ethanol may be used in the eluant systems.

Uses:

Compositions from shark cartilage produced by methods of the present invention are useful for stimulating the cellular and humoral components of the immune system. Thus, the compositions may be useful for treating or preventing tumor growth, bacterial infections, viral infections and/or fungal infections. Specifically, the compositions have significant stimulatory activity for mouse spleen B cells and NK cells, as well as for mouse peritoneal macrophages, when added to these cells in tissue culture. Macrophages are the first link in the immune response chain since they scavenge antigens, process them, and present the peptides from those antigens thereby activating the immune response cascade; B cells produce antibodies, and NK cells are vital in protection from tumors.

The shark cartilage compositions of the present invention may be used as such or they may be formulated into formulations. Formulations may be for enteral (e.g. oral), rectal, parenteral or other modes of administration. The formulations comprise the composition of the present invention in combination with one or more physiologically acceptable ingredients, such as carriers, excipients and/or diluents. Compositions and formulations for oral administration are particularly preferred.

Formulations may be prepared, for example, in unit dose forms, such as tablets, capsules, dragees, suppositories or ampoules. They may be prepared in a conventional manner, for example by means of conventional mixing, granulating, confectioning, dissolving or lyophilising processes.

To prepare formulations of the present invention in the form of dosage units for oral administration, the shark cartilage compositions of the present invention may take the form of, for example, granules, tablets, capsules, liquids or dragees prepared together with physiologically acceptable carriers, excipients and/or diluents.

Typical physiologically acceptable ingredients include:
(a) binding agents such as starch (e.g. pregelatinised maize starch, wheat starch paste, rice starch paste, potato starch paste), polyvinylpyrrolidone, hydroxypropyl methylcellulose, gum tragacanth and/or gelatin;
(b) fillers such as sugars (e.g. lactose, saccharose, mannitol, sorbitol), amylopectin, cellulose preparations (e.g. microcrystalline cellulose), calcium phosphates (e.g. tricalcium phosphate, calcium hydrogen phosphatelactose) and/or titanium dioxide;
(c) lubricants such as stearic acid, calcium stearate, magnesium stearate, talc, silica, silicic acid, polyethylene glycol and/or waxes;
(d) disintegrants such as the above-mentioned starches, carboxymethyl starch, cross-linked polyvinylpyrrolidone, agar, alginic acid or a salt thereof (e.g. sodium alginate) and/or sodium starch glycollate;
(e) wetting agents such as sodium lauryl sulphate; and/or,
(f) stabilizers.

Soft gelatin capsules may be prepared with capsules containing a mixture of the shark cartilage composition together with paraffin oil, liquid polyethylene glycols, vegetable oil, fat and/or another suitable vehicle for soft gelatin capsules. Plasticizers such as glycerol or sorbitol may also be used. Hard gelatin capsules may contain granules of the composition. Hard gelatin capsules may also contain the composition in combination with solid powdered ingredients such as those listed above.

Liquid formulations for oral administration may be prepared in the form of solutions, syrups or suspensions. Liquid formulations typically comprise the shark cartilage composition together with an excipient such as sugar or sugar alcohols, and a carrier such as ethanol, water, glycerol, propylene glycol, polyethylene glycol, almond oil, oily esters or mixtures thereof. If desired, such liquid formulations may also contain coloring agents, flavoring agents, saccharine, thickening agents (e.g. carboxymethyl cellulose), suspending agents (e.g. sorbitol syrup, methyl cellulose, hydrogenated edible fats), emulsifying agents (e.g. lecithin, acacia), and/or preservatives (e.g. methyl p-hydroxybenzoates, propyl p-hydroxybenzoates, sorbic acid). Liquid formulations for oral administration may also be prepared in the form of a dry powder to be reconstituted with water or another suitable vehicle prior to use.

An immunomodulating effective amount of the shark cartilage composition may depend on various factors, such as the method of administration, species of animal, age and/or individual condition. The composition may be administered in a range of about 50-5000 µg/day. In a normal case, the approximate estimated daily dose for a human patient weighing approximately 75 kg is about 200-400 mg. The composition may be administered once per day or multiple times per day.

BRIEF DESCRIPTION OF THE DRAWINGS

The invention will now be described by way of example having regard to the appended drawings in which.

EXAMPLES

Figure 1A:
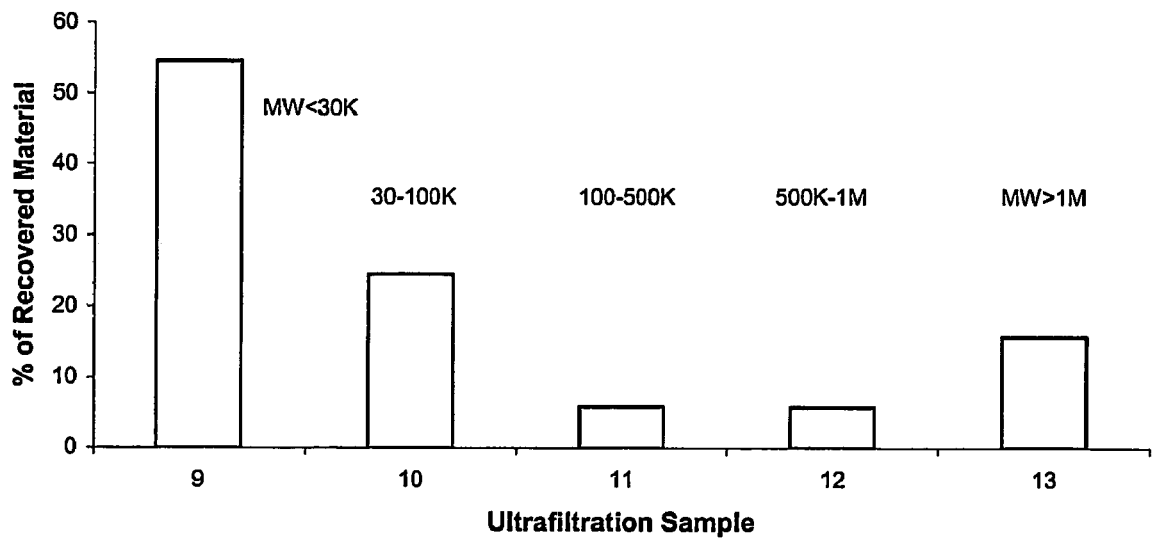
FIG. 1A is a graph showing yields of fractions from ultrafiltration of (concentrated) shark cartilage extract 3. In Series a, 2 M guanidine hydrochloride was used as the eluent; 64 ml of the solution containing 2.8 g was loaded to the ultrafiltration cell.

Materials and Methods:

All chemicals were of analytical grade and were purchased from Sigma Aldrich, (Milwaukee, Wis.), unless specified otherwise. The cartilage was obtained from healthy sharks (dog fish, *Squalus acanthias*) by freeing the cartilage of any adherent muscle or connective tissue and scraping it clean with scalpels and scissors. It was then stored at −80° C., until use. The cartilage was dried and pulverized to a mean particle size of 35 μm. The Amicon™ ultrafiltration cell (450 ml volume), and ultrafiltration membranes (76 mm in diameter) were obtained from Pall Corp (Mississauga, ON). Dialysis membranes (MWCO 12 KD) were obtained from Sigma Aldrich. All chromatography was performed using Pharmacia columns and matrices (Pharmacia, Uppsala, Sweden). RPMI 1640 medium was obtained from Gibco-BRL (Invitrogen Life Technologies, Burlington, ON). The BCA kit for protein determination was purchased from Pierce (Rockford, Ill.). Costar™ 3950 ELISA and tissue culture plates were purchased from Fisher Scientific (Halifax, NS). Anti-Thy-1.2-coated and anti-B220 (anti-CD45R) Miltenyi™ microbeads and MidiMACS™ columns and magnets were supplied by Miltenyi™ Biotek (Auburn, Calif.). All lyophilized extracts and fractions were obtained in the form of white, fluffy, flaky materials, unless specified otherwise.

Extraction:

Method A

Twenty grams of pulverized shark cartilage were suspended in 100 ml guanidine medium (4 M guanidine hydrochloride, 0.01 M Na$_2$EDTA, 0.1 M 6-aminohexanoic acid, 0.05 M sodium acetate, 0.001 M benzamidine hydrochloride, 0.01M N-ethylmaleimide, 0.001 M phenylmethylsulfonyl fluoride and 0.02% sodium azide, pH 6.0), and gently stirred at 4° C. for 24 hours. The solids were centrifuged (17,500×g, 30 min), washed, and the combined supernatant was dialyzed against distilled water. After clearing by centrifugation the resulting material was lyophilized to obtain 1; yield 1.1 g, 5.25%.

Method B

Twenty grams of pulverized shark cartilage were suspended in 100 ml of guanidine medium (2 M guanidine hydrochloride in 0.02 M MOPS, pH 6.5) and gently stirred at 4° C. for 72 hours. The solids were centrifuged (13000×g, 30 min.), washed, and the combined supernatant was dialyzed against 0.15 M NaCl in 0.05 M Tris buffer, pH 7.5. After clearing by centrifugation the resulting material was precipitated under gentle stirring with cold ethanol (final ethanol concentration of 80%) and left in the fridge overnight. The solids were filtered off, dissolved in the smallest volume of the above Tris buffer and dialyzed against distilled water. The sample was cleared by centrifugation and lyophilized to obtain 2; yield 0.61 g, 3.0%.

Method C

Three hundred grams of pulverized shark cartilage were suspended in 1500 ml of distilled water and extracted at 80-85° C. for 1 hour. The solids were then removed by centrifugation (3000×g, 30 min) and the pellet was washed twice with 400 ml of distilled water. The volume of the combined liquids was reduced by evaporation under vacuum to 500 ml and the concentrate was split into five equal portions that were treated as follows:

The first portion was directly lyophilized to obtain 3; yield 5.61 g, 9.4%.

The second portion was dialyzed against a 12 KD MWCO membrane and the dialyzed material was then lyophilized to obtain 4; yield 4.36 g, 7.3%.

The third portion was treated with ammonium sulfate (the final concentration of 40%) and gently stirred at 4° C. for 16 hours. The solids were centrifuged off (18000×g, 2×30 min.). The pellet was re-dissolved in 30 ml of distilled water, the material was dialyzed and finally freeze-dried to obtain 5; yield 2.63 g, 4.4%. The supernatant was also dialyzed and freeze-dried to obtain 6; yield 0.30 g, 0.5%.

The fourth portion was mixed with ethanol under stirring (the final ethanol concentration was 80%) and then gently stirred for 16 hours at 4° C. The solids were filtered off and washed with 50-70 ml of absolute ethanol. The filter cake was then re-dissolved in 50 ml of distilled water, and the solution was dialyzed and finally freeze-dried to obtain 7; yield, 3.41 g, 5.7%. The supernatant was dialyzed and freeze-dried to obtain 8; yield, 0.37 g, 0.6%.

The fifth portion was ultrafiltered as described below.

Ultrafiltration:

The fifth portion from the initial extraction procedure described above (Method C) was divided into two equal parts: one was dissolved in 2 M guanidine hydrochloride (Series a), the other one in water containing 0.02% sodium azide (Series b). Both solutions were fractionated under equal conditions. The yields of the fractionations are listed in FIG. 1A. Each solution was passed through a 30 KD membrane under 35 psi of nitrogen pressure until the volume of the retainate was 20 ml. Then the retainate was washed 10 times with 50 ml of 2 M GuCl (or 0.02% sodium azide); each wash was pushed through the membrane until the volume of the retainate was reduced to 20 ml and the filtrate was dialyzed against distilled water and lyophilized, yielding materials 9a,b. The thoroughly washed retainate was then passed in a similar manner through a 100 KD membrane, and the filtrate was dialyzed and lyophilized as above, yielding materials 10a,b. The resulting retainate was passed successively through a 500 KD and a 1000 KD membrane, giving 11a,b and 12a,b, respectively. Finally, the retainate was dialyzed and lyophilized to give 13a,b. The efficiency of the ultrafiltration was monitored spectrometrically to assure that the UV$_{280}$ absorbance of final washes did not exceed 0.03.

Determination of Optimum Ammonium Sulfate Concentration:

A solution of 3 was concentrated by rotary evaporation to 50 mg/ml, split into eight equal parts, and these were treated under gentle magnetic stirring with solid ammonium sulfate. The final concentration of the precipitant ranged from 15-45% in 5% increments, and a control portion containing no ammonium sulfate was included. The mixtures were stirred for 16 hours at 4° C., then centrifuged at 20700×g for 30 min to separate the supernatants from the pellets. The pellets and the supernatants were dialyzed separately against water and lyophilized.

Preparative Chromatography:

Sephadex™ G-100

The starting material (4, 1.0 g) was applied on a Sephadex™ G-100 column (2.6×100 cm) and eluted with 1 M sodium formate, pH 3.5, at a flow rate of 24 ml/h. The fractions were monitored at 280 nm and after mixing with phenol sulfuric acid reagent they were retested at 490 nm [22]. The materials were resolved into two major peaks 14 (high molecular mass peak) and 15 (low molecular mass peak).

Sephacryl™ S-300 HR

The starting material (4, 14, 1.0 g) was applied on a Sephacryl™ S-300 HR column (2.6×100 cm) and eluted with 1 M sodium formate, pH 3.5, at a flow rate of 24 ml/h. The fractions were monitored as above. The materials were resolved into two major peaks 16, 17 (originating from 4), and 18, 19 (originating from 14), respectively.

DEAE Sepharose™

The starting material (14, 30 mg) was applied on the column of DEAE Sepharose™ (1.0×20 cm) and eluted with 0.1 M sodium acetate in 10% ethanol, pH 4.4 with a linear gradient of NaCl (0.15-3.0 M), at a flow rate of 4 ml/hr. The fractions were monitored as above. The material was resolved into three major peaks 20, 21 and 22.

Analysis:

Protein Determination

The protein determination of the samples was carried out using the BCA method [35] according to the instructions accompanying the kit in a 96-well ELISA microtitre plate format.

Amino Acid Analysis

Samples were hydrolyzed in 6M HCl under vacuum at 110° C. for 20 hours, using norleucine as an internal standard. Analysis was performed on a Beckman system 6300, using the Beckman 4×120 mm Na-high performance hydrolysate column (cation exchange).

Uronic Acid Content Determination

Quantitative and qualitative determination of uronic acids content was performed according to Blumenkrantz and Asboe-Hansen [36]. Fresh m-hydroxydiphenyl reagent was used for each analysis.

N-acetylamino Sugar Content

Quantitative and qualitative determination of N-acetylamino sugar content was performed according to Reissig et al using GalNAc and GlcNAc as standards and DMAB reagent [37].

Determination of Proteoglycan Concentration

Proteoglycan content was determined using DMB as described by Farndale et al [38]. Chondroitin sulfate A was employed as the standard.

Stimulation of Splenocyte Proliferation

Mouse splenocytes were isolated as previously described [39]. The cells were plated at $3\times10^5$ cells/well in in 0.1 ml of cRPMI medium (cRPMI=complete RPMI: 90 ml RPMI 1640, 10 ml fetal calf serum, 1 ml Penicillin/Streptomycin [10,000 U/ml P, 100 µg/ml S], 1.0 ml of 0.2 M glutamine, 1.5 ml of 1 M Hepes, 0.1 ml of 2-mercaptoethanol) in 96-well flat bottom tissue culture plates. Then 100 µl of each test sample in the cell medium were added to triplicate wells. The plates were covered with sterile lids and incubated in 5% $CO_2$ and 100% humidity at 37° C. in a $CO_2$ incubator for 48 hours. The cells were then pulsed with $^3$H-thymidine (1 µCi/well in 10 µl cRPMI) and after incubating as above for another 18 hours they were harvested with an automated cell harvester. The filter strips were allowed to dry for 3 h at 37° C., the discs were removed from the filter strips and placed in scintillation vials with 7.0 ml of counting fluid and the radioactivity was then determined.

Isolation of B-cells and T-cells from Splenocytes

Mouse splenocytes were isolated as above and placed in tissue culture flasks at 37° C. for 2 hours, to allow the macrophages to settle and adhere to the flask. The suspended lymphocytes were then removed, centrifuged, re-suspended in a small amount of cold PBS-EDTA-BSA buffer (PBS with 2 mM EDTA and 0.5% BSA, pH 7.4), placed on ice, counted and re-centrifuged. Finally, they were re-suspended at a concentration of $3\times10^7$ cells/ml in the buffer.

a) Negative isolation of B cells: One hundred microliters of anti-Thy-1.2-coated Miltenyi™ microbeads were added, and the mixture was incubated for 20 min. Then 5.0 ml of PBS-EDTA-BSA were added and the suspension was pipetted into a midiMACS™ column in a midiMACS™ magnet. The T-cells adhered to the column while the B cells passed through and were collected. Without removing it from the magnet, the column was rinsed with 5.0 ml of the buffer to remove any residual B-cells. The B-cells were combined, spun, re-suspended in 1 ml of cRPMI and counted. They were then diluted to $5\times10^6$ cells per ml of cRPMI and plated at 100 µl/well for stimulation assays.

b) Negative isolation of T cells: The same procedure was followed except the magnetic beads used for the incubation were coated with anti-B220 instead of anti-Thy-1.2 antibody.

Nitrite Assay for Mouse Peritoneal Macrophages

Mice were euthanized by cervical dislocation. Peritoneal macrophages were obtained by peritoneal lavage with 10 ml of ice cold cRPMI injected into the peritoneal cavity. The obtained macrophages were centrifuged for 10 min at 400×g and re-suspended for counting. They were then re-suspended to $1\text{-}2\times10^6$ cells/ml of cRPMI-1640, and then plated into a 96-well tissue culture plate at $1\times10^5$ cells/well in a 100 µl volume. Test samples were added in cRPMI (100 µl) with and without IFN-γ. The positive controls were the cells plus IFN-γ (2 U/well), and LPS plus IFN-γ. After incubating for 48 h in 5% $CO_2$, 50 µl of the culture fluid (LPS, 20 ng/well; IFN-γ, 2 U/well) were collected and transferred to wells in a 96-well flat bottom ELISA plate. Twofold serial dilutions of $NaNO_2$ (125 µM to 1 µM final concentration) in cRPMI were made, and added to a set of wells to provide a standard curve, along with 50 µl of Greiss Reagent solution each. A plot of absorbance values at 550 nm against $NaNO_2$ concentrations was made. The standard curve was used to determine the amount of $NO_2^-$ produced by the peritoneal macrophage samples.

Stimulation of Cytokine Production by Mouse Splenocytes and Determination of Cytokines with ELISA The tested substances were added at several concentrations to the cells in 96-well tissue culture plates and incubated for 24-48 hours, depending on the cytokine of interest. The supernatant culture fluid was removed and assessed by adding to 96-well ELISA plates coated with the appropriate anti-cytokine monoclonal antibody, in 50 mM carbonate buffer, pH 9.6 at 4° C. overnight. The plates were then washed with TBS (2.4 g Trizma™ base, 8.0 g NaCl and 0.2 g KCl per liter, pH 7.4), post-coated with 2 mg/ml BSA in TBS (200 µl/well) for 2 hours at room temperature, and washed with TBS/Tween™ (0.05%). One hundred µl of the unknown samples, and the standards diluted serially from 1 ng/ml to 15 µg/ml in TBS/Tween™ containing 0.1% BSA, were added to the coated ELISA plates, and incubated overnight at 4° C. After washing with TBS-Tween™, 100 µl of the appropriate biotinylated anti-cytokine mAb in PBS/Tween™, containing 0.1% BSA, was added to each well. After incubation at room temperature for 1 hour, the plates were washed with TBS/Tween™. Extravidin peroxidase in PBS/Tween™ containing 0.1% BSA was added (100 µl/well). After incubating at room temperature for 30 min, the plates were washed and 100 µl/well of TMB substrate solution was added. After 10 to 30 min incubation, depending on color development, the reaction was quenched with 100 µl/well of 1 M $H_3PO_4$, and the plate was read at 450 nm.

Effect of the Extract on Proliferation of *Listeria monocytogenes* in Infected Mice Two doses of the lyophilized extract 4 prepared in accordance with Method C (0.1 mg or 4 mg) or plain water were administered to Balb/c mice by intragastric tube three times a week for four weeks. The mice were then infected by intravenous injection of 5000 viable *Listeria monocytogenes* organisms. Three days after the injections of the *Listeria* the mice were sacrificed, and cell suspensions of their spleens were made and cultured on culture dishes to determine the number of bacteria in the spleens of the control water fed mice and in the spleens of the mice fed with the shark cartilage extract.

Results:

Extraction

Extraction with guanidine based media or hot water yielded materials stimulating proliferation of splenocytes in vitro. Hot water extractions delivered products in higher yields. Although the products obtained from guanidine based media extractions had higher proportions of proteoglycans, as seen from the uronic acid and aminosugar contents as well as from their interaction with DMB, they displayed comparable immunoactivities with those isolated from hot water extracts. The average yields of the extractions and the immunoactivities of the produced extracts in vitro as tested on undifferentiated spleen cells are shown in Table 1. Table 1 provides the yield, the index of proteoglycan content, the uronic acid content and immunoactivity in vitro of shark cartilage extracts produced by Methods A, B and C. The index of proteoglycan content is defined as the ratio of the sample's proteoglycan content to the proteoglycan content of the supernatant of 40% ammonium sulfate precipitation. Uronic acid content is defined as µg glucuronic acid/µg sample material. Immunoactivities are defined as the cell proliferation due to each sample relative to the cell proliferation due to cartilage extracted with 2 M GuCl (2). The samples were tested for immunoactivity at a concentration of 125 µg/ml.

TABLE 1

Comparison of three methods of extraction of immunoactive principles of shark cartilage.

| method | material | yield (%) | index of proteoglycan content | uronic acid content | immunoactivity (%) |
|--------|----------|-----------|-------------------------------|---------------------|--------------------|
| A | 1 | 4.1 | 0.80 | 0.10 | 82.3 |
| B | 2 | 3.7 | 0.59 | 0.14 | 100 |
| C | 3 | 9.4 | 0.37 | 0.07 | 44.2 |
| C | 4 | 7.3 | 0.34 | 0.08 | 78.2 |

For extraction Method C, four alternatives producing extract materials 3, 4, 5, 6, 7 and 8 were compared with respect to yield and immunoactivity. Table 2 provides the results. Immunoactivities were tested at a sample concentration of 125 µg/ml and are compared to the activity of product 2, taken as 100%.

TABLE 2

Comparison of methods for isolation of immunoactive components of hot water extract (Method C).

| Method | Material | Yield (%) | Immunoactivity (%) |
|--------|----------|-----------|--------------------|
| C i | 3 | 9.4 | 44.2 |
| C ii | 4 | 7.3 | 78.2 |
| C iii | 5 | 4.4 | 92.4 |
| C iii | 6 | 0.5 | 7.0 |
| C iv | 7 | 5.7 | 80.9 |
| C iv | 8 | 0.6 | 0.1 |

Salting Out and Ethanol Based Fractionations

The active principles were precipitated from the mixtures containing more than 25% of ammonium sulfate. The immunoactivity of the pellets remained unchanged whereas the activity of the supernatants progressively decreased with increased concentration of ammonium sulfate. To obtain the highest yields of the precipitate generated from a 50 mg/ml concentration of 3 at least 35% of ammonium sulfate in the final mixture was necessary. To compensate for the variance in the starting materials we used 40% of ammonium sulfate. Although the yields of the ammonium sulfate based precipitations were compromised, the lyophilized supernatants had the highest glycosaminoglycan/proteoglycan content and were associated with the highest immunoactivities.

Ethanol was also examined to precipitate the immunoactive principles from concentrated hot water extracts. This method of precipitation results in higher yields and represents a simple method requiring no complicated equipment and it could be easily scaled up. The yields and changes in the specific immunoactivity in vitro are listed in Table 2.

Ultrafiltration

Figure 1B:
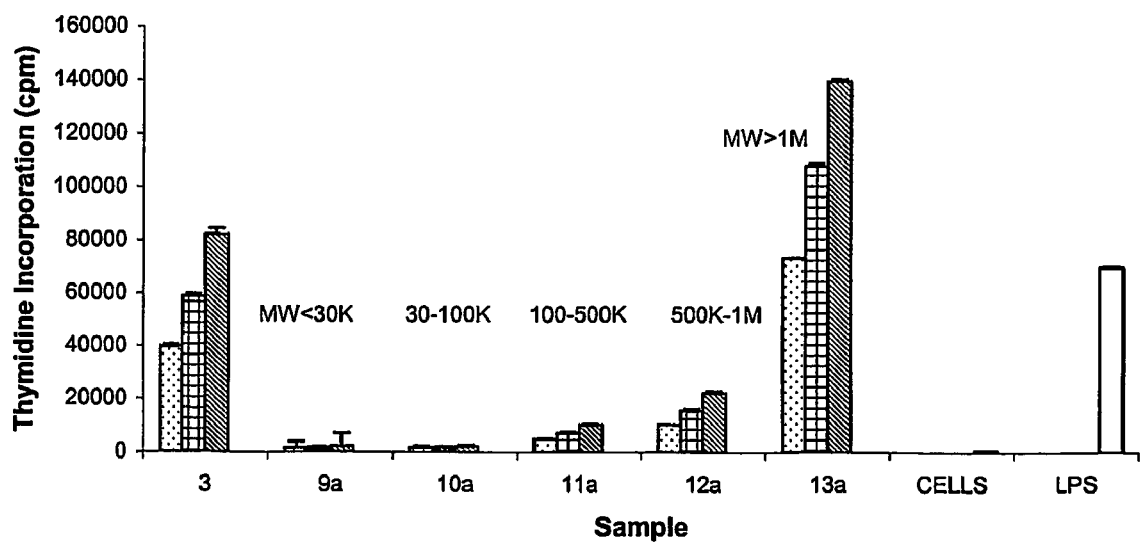
FIG. 1B is a graph showing immunoactivities in vitro of molecular weight fractions from ultrafiltration (guanidine hydrochloride) of concentrated extract 3 as measured by thymidine incorporation. Three different concentrations of sample are shown: 31.25 µg/ml: ▫; 62.5 µg/ml: ⊞; 125 µg/ml: ▨. Controls were untreated cells (negative control) and cells challenged with 20 µg/ml LPS (positive control); they are denoted by ▫. Samples shown are 3: undialyzed and lyophilized; 9a: MW<30 KD; 10a: 30-100 KD; 11a: 100-500 KD; 12a: 500-1000 KD; 13a: MW>1000 KD. 9-13 are all dialyzed against a MWCO 12 KD membrane in water and lyophilized.

Much of the material dissolved in 0.02% sodium azide passed through a 30 KD membrane. Further experiments revealed that while almost all the molecules (or molecular assemblies) in the previously dialyzed extract were smaller than 1 MD, the bulk of the activity of the extract is contained in the largest molecules or molecular assemblies, i.e., those larger than 1 MD. The relevant literature dealing with SEC of PGs indicates that nonspecific adsorption is pH dependent and decreases in the presence of detergents or chaotropic agents (40). Bearing this in mind, we conducted further studies in the presence of 2 M guanidine hydrochloride. The results showed that under the conditions of exhaustive dialysis the yields of ultrafiltration did not significantly differ from those employing water preserved with sodium azide. The immunoactivity of the samples was again detected almost entirely in a region above the 100 KD range and particularly for molecules with a molecular mass greater than 1 MD (FIG. 1B).

Chromatography

Size exclusion and anion exchange chromatography were executed on the crude extracts (i.e. on 4) and on selected more defined products. The eluted fractions were monitored at 280 nm for the presence of protein or protein moieties, and at 490 nm (after reaction with phenol/sulfuric reagent) for the presence of carbohydrates or carbohydrate moieties. In accordance with prior art methods, monitoring at 218 nm (absolute maximum obtained by scanning a non-chromatographed sample within 200-700 nm range) may also be done. It is close to the absorbance range used typically for monitoring proteoglycans (206-214 nm) [40]. Although only a small local maximum at 280 was observed compared to that of BSA, it was very useful for monitoring the chromatography.

A solution of bovine cartilage collagen available to us was also scanned for comparison since a significant amount of collagen was expected to be present in 4, however, due to high absorbance background at the wavelengths beyond 220 nm, no useful information was gained.

Size Exclusion Chromatography

Figure 2:
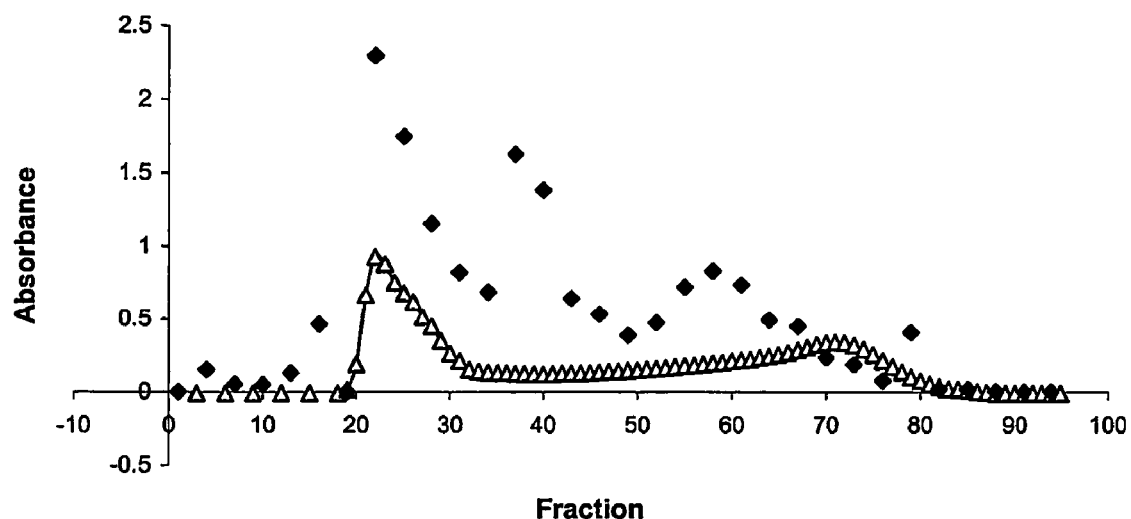
FIG. 2 shows Sephadex™ G-100 size exclusion chromatography of extract 4. Fractions were monitored at 280 nm (Δ), and at 490 nm after mixing with phenol-sulfuric acid reagent (♦). One gram of sample was eluted with 1 M sodium formate, pH 3.5, at a flow rate of 24 ml/h, through a column of dimensions 2.6×100 cm.

One molar ammonium acetate, pH 6.0, resolved the crude extracts into two major peaks on Sephacryl™ S-300 HR. Surprisingly, Sephadex™ G 100, a matrix with a lower resolution range, resolved the extracts similarly into two peaks with apparently equal efficiency. Sephadex™ G-100 chromatography of dialyzed crude extracts, passed through 100 KD ultrafiltration membrane, demonstrated the competence of the ultrafiltration process. When the retained portion was chromatographed only one peak was found. When the filtrate was subjected to chromatography, a very broad peak with a small peak attached were found, confirming the presence of low molecular mass fractions contaminated only with a small portion of the high molecular mass compounds. Ammonium acetate caused problems due to its volatility under vacuum during degassing and later on was replaced with sodium acetate. Low pH also helped resolution and the concentration of the salt was found to be important; e.g. solutions lower than 0.5 M performed poorly. Final conditions for SEC utilized either 1 M sodium acetate, pH 4.4, or, preferably, 1 M sodium formate pH 3.5 (FIG. 2).

Ion Exchange Chromatography

Figure 3:
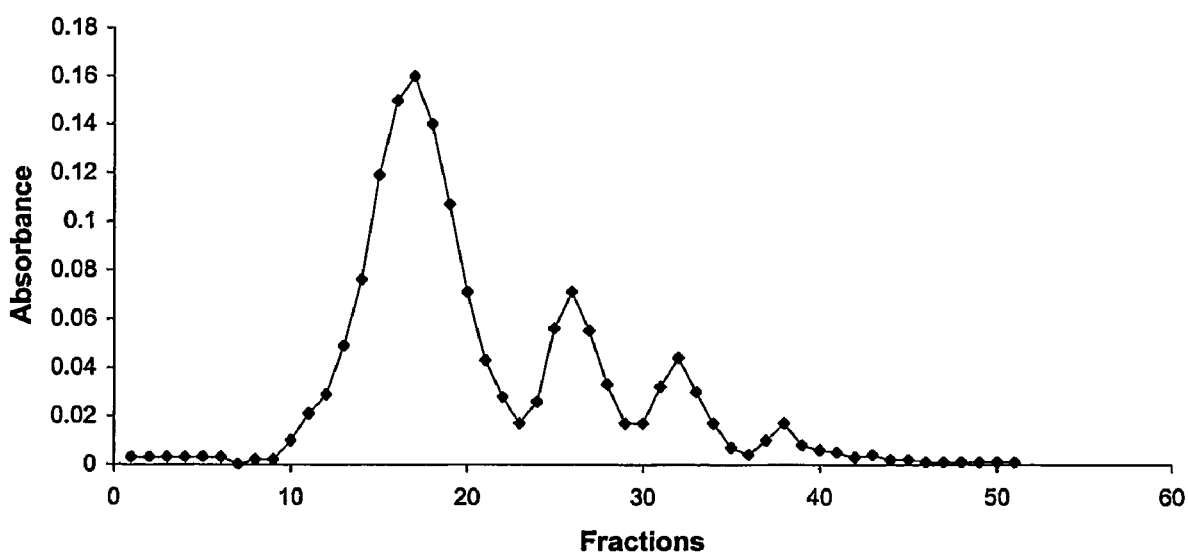
FIG. 3 shows DEAE Sepharose™—Fast Flow ion exchange chromatography of extract 4. Initial eluent was 0.1 M sodium acetate, pH 4.4 with 0.15 M sodium chloride and 10% ethanol. Then the sodium chloride concentration was increased in a gradient up to 3 M. Flow rate was 4 ml/h through a column of dimensions 1×20 cm.

Our best performing system was a linear gradient of NaCl (0.15 to 3 M) in 0.1 M acetate buffer, pH 5.6. Although this system worked with DEAE Sepharose™, there were concerns with its reproducibility. By adding 10% EtOH in the eluent and by lowering pH to 4.4, noncovalent intermolecular interactions were significantly reduced (FIG. 3). Proliferation of splenocytes challenged by the materials isolated from the chromatography was examined in vitro. The highest activity was found in the first peak.

Analysis

Amino Acid Analysis

All major amino acids were detected and the presence of D-GlcN and D-GalN was revealed in separate spiking runs. The major amino acids were glycine (15.2%), proline (14.4%), alanine (12.8%), glutamic acid (11.1%), aspartic acid (6.6%) arginine (6.2%), measured as a percentage of total amino acid content. The composition does not differ significantly among the preparations differing in molecular mass range. The only major difference was that 3, 5, and 8 contained about twice as much glycine as the dialyzed water extract 4 or the pellet obtained from EtOH precipitation (7).

Proteoglycan Determination

Figure 4:
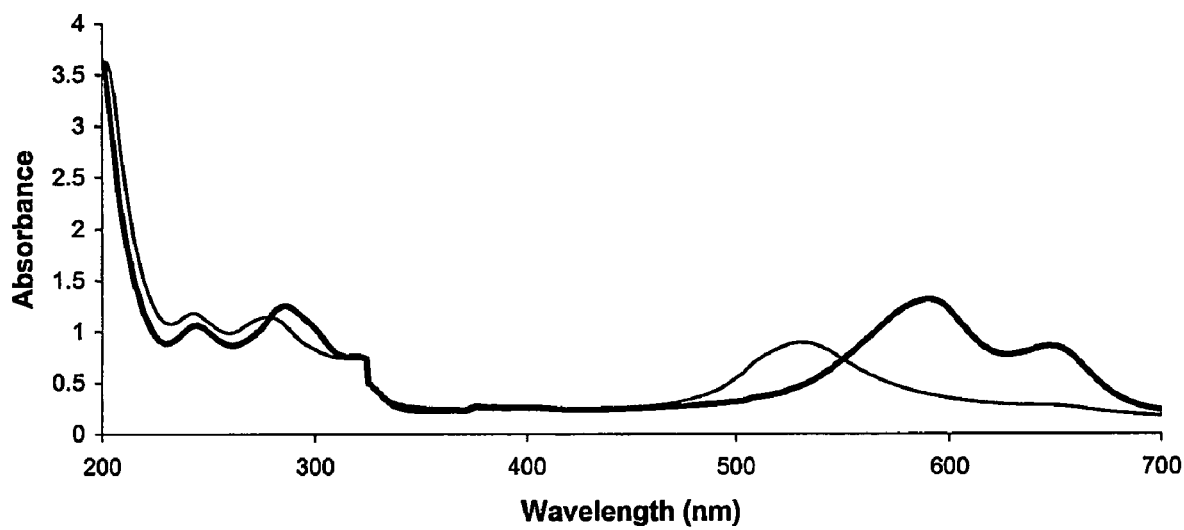
FIG. 4 is spectrometric scans of DMB (16 µg/ml) before (-) and after (-) complexation with extract 4 (100 µg/ml, from 200-700 nm).

Detection of PGs/GAGs was based on the metachromatic shift of the 590 nm peak of DMB solution to 525 nm after complexation with PGs or GAGs. This approach is a modification of a method described by Chandrasekhar [41] and facilitates rapid detection of PGs (FIG. 4). Several standard curves (originally for fractions obtained from every type of process (chromatography, ultrafiltration, salt precipitation, etc) were generated. After carefully examining these curves, it was decided to use as the standard a CHS curve, defined by the equation: $y=0.0023x-0.0195$ ($R^2=0.9977$) in the concentration range 25-100 µg/ml.

Assessment of Stimulation of Lymphocyte Proliferation

Figure 5:
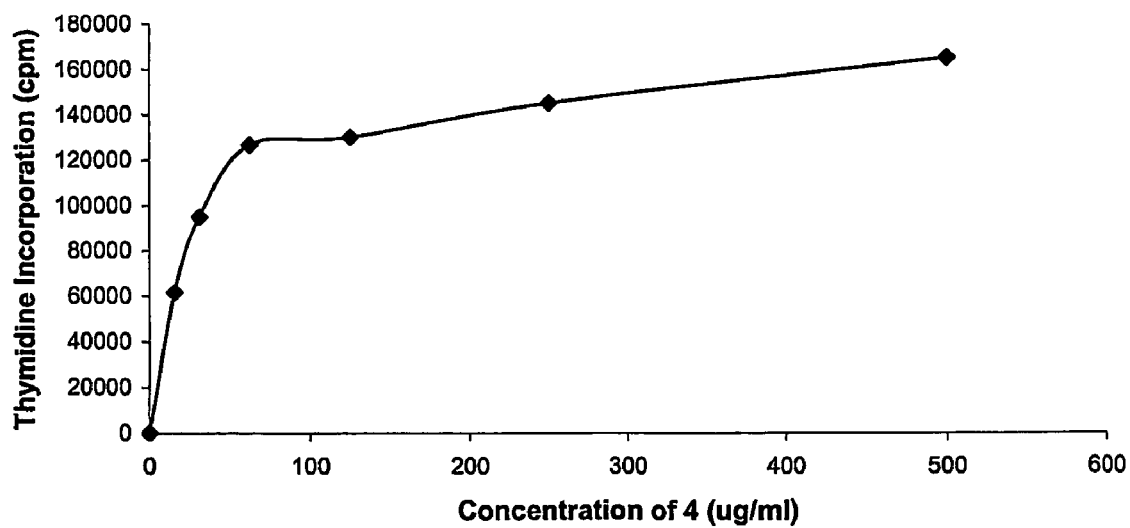
FIG. 5 is an example of a titration curve generated as a relationship between the concentration of tested substance and immunoactivity in vitro. The immunoactivity in vitro was measured by thymidine incorporation.

Since LPS (a powerful stimulant of lymphocyte proliferation) is a potential contaminant of biological extracts, it was essential to verify that the results were not being confounded by LPS contamination [42]. BALB/c strain, as most strains, is sensitive to LPS, so the effect of polymyxin B, a potent inhibitor of LPS on the mitogenic activity of the extracts [43, 44] was assessed. In some instances the extracts were also tested on spleen cells from C3H/HeJ (insensitive to LPS strain) mice [45]. No significant differences have been found in the stimulation of BALB/c and C3H/HeJ spleen cells. Important preparations were tested at a number of concentrations in order to obtain for each sample a "titration" curve to allow a more accurate comparison of mitogenic activities between different samples (FIG. 5).

Figure 6:
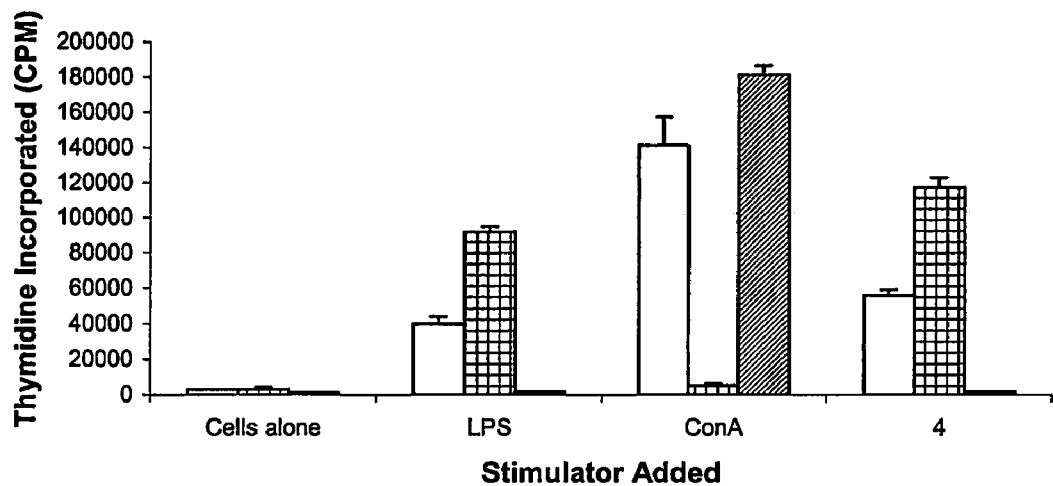
FIG. 6 is a graph showing proliferation of subpopulations of spleen cells (B cells and/or T cells) in the presence of 4. LPS was used as a B-cell stimulator whereas ConA was used as a T cell stimulator. Mixed spleen cells: ▫; purified B cells: ⊞; purified T cells: ▨.

Effect of the Shark Cartilage Preparations on Purified Populations of B Cells, T Cells, Macrophages, and NK Cells Samples of the purified cells were tested for mitogen responsiveness and by flow cytometry. As can be seen in FIG. 6 from a representative mitogen stimulation assay of 4, the results with purified populations of cells show that the B lymphocytes are targets for induction of proliferation by the materials present in the shark cartilage preparations, whereas the T lymphocytes are not stimulated significantly. In addition it was found that macrophages were stimulated. This was of considerable interest since macrophages play a number of critical roles in the immune response.

Figure 7:
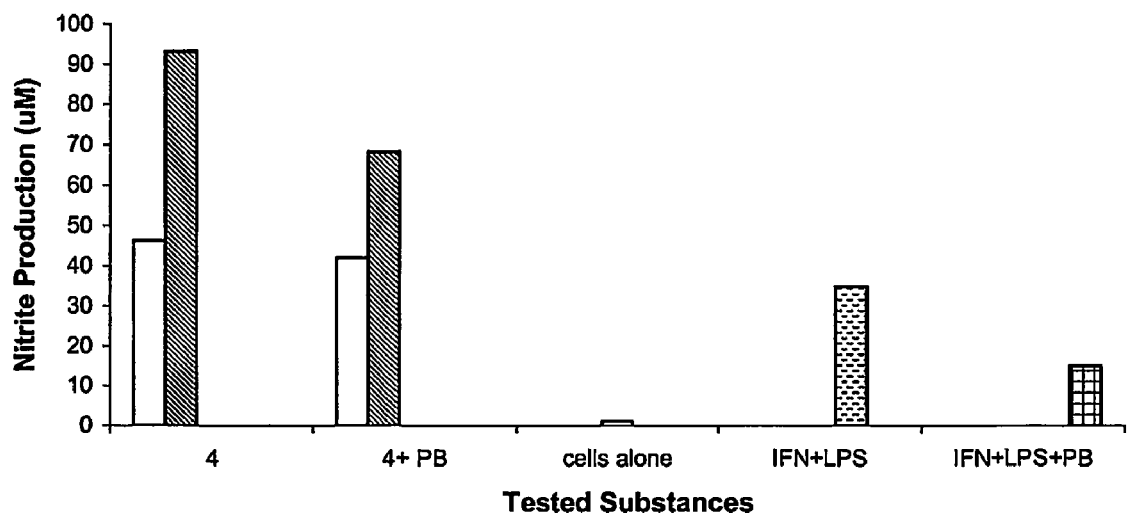
FIG. 7 is a graph showing stimulation of macrophages challenged with 4, as measured by production of nitric oxide. The sample was tested at a concentration of 125 µg/ml (▫) and 500 µg/ml ▨. Cells alone were used as a negative control.

Purified mouse macrophages cultured with the extracts produced significantly higher levels of nitrite than macrophages challenged with a PBS blank. In FIG. 7 a typical result is shown, including the evidence that the stimulation was not significantly affected by polymyxin B. Macrophages are also known to be stimulated by LPS. For example, extract 4 at two different concentrations markedly increased nitrite production by purified macrophages, and this increase was not significantly affected by the presence of polymyxin B. Conversely, although the combination of LPS and interferon γ also stimulated nitrite production, the LPS stimulation was substantially reduced in the presence of polymyxin B.

Figure 8:
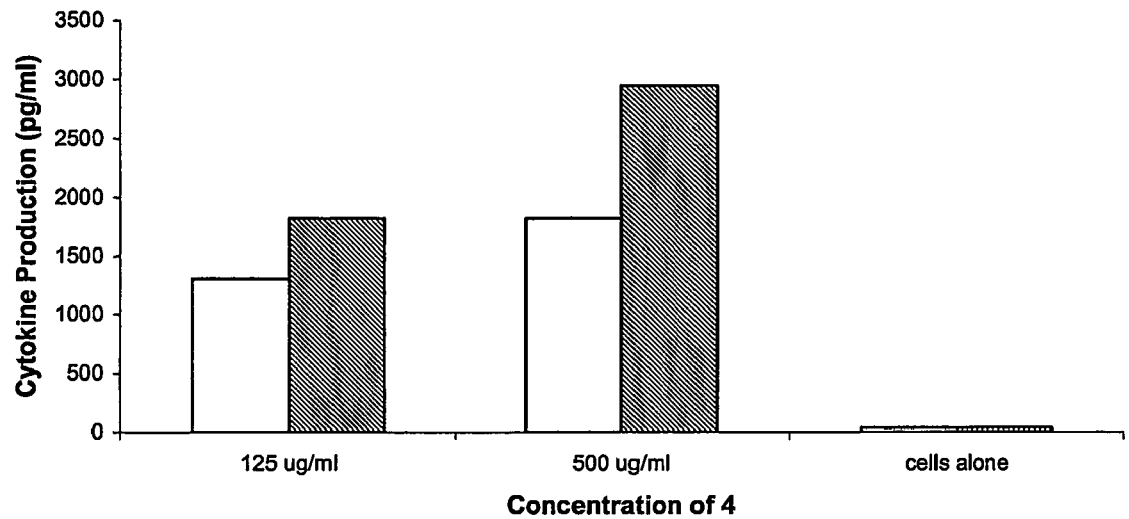
FIG. 8 is a graph showing stimulation of macrophages by shark cartilage extract, determined by release of cytokines IL-6 ▨ and IL-12 (▫). Production of IL-6 and IL-12 was measured by sandwich ELISA.

Additional experiments were carried out to further characterize the ability of the cartilage preparations to induce macrophage activation. The results confirmed that the preparations were potent inducers of macrophage activation and that this activation is greatly potentiated by co-incubation with INF-γ. Also investigated was whether the stimulation of nitrite production was due to an increase in the production per cell, or due to stimulation of proliferation of the macrophages. It was found that the extracts had no mitogenic effect on macrophages (i.e. they did not induce macrophage proliferation). The patterns of production of a number of cytokines induced by shark cartilage extract activation were examined, and an increase in production of IL-1, IL-6, IL-10, and IL-12 was demonstrated. FIG. 8 shows the strong stimulatory effect of shark cartilage extracts on macrophage IL-12 and IL-6 production, again demonstrating dose-related responses.

Effect of Feeding the Shark Cartilage Extracts on Susceptibility to Infection with *Listeria monocytogenes*

Figure 9:
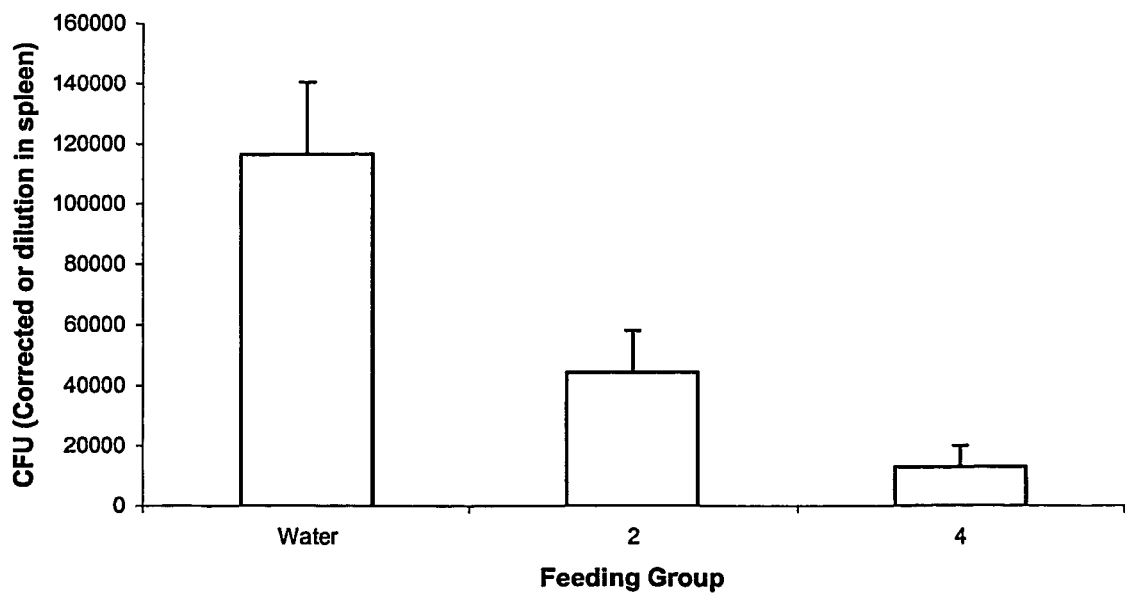
FIG. 9 is a graph showing a protective effect of feeding mice with 2, 4 or water from *Listeria*. Mice received 20 mg of 2 or 4 every second day for three weeks, then they received the lethal dose of pathogen and later sacrificed.

Experiments were carried out on the possible protection from infection in viva, using infection with *Listeria monocytogenes* as a model [46, 47]. There was a significant decrease in the number of *Listeria* colony forming units in the mice fed the different extracts. As shown in FIG. 9 we found that the cartilage extracts (10 mg dose) tested markedly suppressed the severity of the *Listeria* infection in terms of the number of bacterial colony forming units found in the spleen of the fed versus the non-fed animals.

Discussion

In addition to buffered guanidine hydrochloride of various strengths, a number of other salts have been used to extract proteoglycans from cartilage. GuCl is the most popular because the others have very narrow concentration ranges for optimal extraction [32]. We did not find any statistical difference between the activity of the extracts when prepared by the above procedure (use of 2 M guanidine buffered with MOPS) or when prepared with 4 M guanidine based media, as is generally recommended in the literature [32, 48]. This is an interesting finding since it is known that the size of extracted PGs is directly correlated with the concentration of the chaotropic agent [40].

Results obtained from stability studies demonstrated the exceptional thermal stability of the extracts of the present invention. Thus, when extractions were carried out at elevated temperatures or even in boiling water, it was found that the extracts could be produced in even higher yields and comparable in activity to the original, unheated guanidine extracts.

All extracts and their fractions exhibited relatively low UV absorbance at 280 nm and protein determination using the BCA method revealed less than a 25% absorbance value compared to that of the BSA standard. Low UV absorbance would suggest either effectively hindered protein cores of proteoglycans, a low frequency of aromatic residues, or a low protein content within heterogeneous preparations. Since BCA reacts with a tetradentate-$Cu^+$ complex (produced between the peptide bonds of the protein core of PG and $Cu^{2+}$ in the presence of $OH^-$), stereochemical hindrance imposed by surrounding GAG chains could prevent the protein core of PGs from reacting with BCA. This would result in low readings and thus underestimation of the protein content. Interestingly, the protein content of about 25% was also in agreement with data obtained from amino acid analysis. Amino acid experiments indicated that both protein and amino sugars were present in the extract, supporting the presence of PGs. The composition revealing the predominance of glycine and proline suggest that all extracts, including the fractions may contain significant amounts of collagen.

Knowing which specific cell types were being stimulated was important not only for basic scientific reasons, but also because in designing potential combination therapies, combining substances which give complementary stimulation, rather than those which simply stimulate the same cells, are more likely to succeed. Activated macrophages produce nitric oxide, which is a free radical with anti-microbial activity, thus the extracts could play an important role in enhancing the body's defense against bacteria. Cytokines are known to bind to PG both to the core protein and to the GAG chain. The capacity to stimulate production of cytokines by macrophages brings important insights with respect to the underlying mechanisms involved in the immunoenhancing activities of the shark cartilage preparations, since IL-1 has many stimulatory functions both within and outside the immune system. IL-1 promotes an acute phase response and can induce all types of cell proliferation, including tissue repair. This has broad implications, which should be considered for future studies. IL-6 is an important effector molecule involved in B lymphocyte activation and stimulation of antibody production, while IL-12 plays a major role in stimulation of NK cells and in affecting the balance of Th1 and Th2 cells [49]. This is important because Th1 cells are primarily involved in cellular immunity and Th2 cells appear primarily involved in humoral immunity.

REFERENCES

1. Green S (1997) Shark cartilage therapy against cancer. *Nutr Health Forum* 14:1-5
2. Hunt T J, Connelly J F (1995) Shark cartilage for cancer treatment. *Am J Health Syst Pharm* 52:1756-60
3. Mathews J (1993) Media feeds frenzy over shark cartilage as cancer treatment. *J Nat Cancer Inst* 85:1190-1
4. McGuire T R, Kazakoff, Hoie E B, Fienhold M A (1996) Antiproliferative activity of shark cartilage with and without tumor necrosis factor alpha I human umbilical vein endothelium. *Pharmacotherapy* 2:237-44
5. Lane J W (1991) Method and dosage unit for inhibiting angiogenesis or vascularization in animals using shark cartilage. U.S. Pat. No. 5,075,112
6. Folkman J, Klagsbrun (1987) Angiogenic factors. *Science* 235:442-7
7. Lee A, Langer R (1983) Shark cartilage contains inhibitors of tumor angiogenesis. *Science* 221:1185-7
8. Dupont E, Brazeau P, Juneau C (1997) Extracts of shark cartilage having an anti-angiogenic activity and an effect on tumor regression: process of making thereof. U.S. Pat. No. 5,618,925
9. Markman M (1996) Shark cartilage: the Leatrile of the 1990. *Clev Clin J Med* 63:179-80
10. Lane I W, Contreras E. High rate of bioactivity (reduction in gross tumor size) observed in advanced cancer patients treated with shark cartilage material. *J Neuropath Med* 1992; 31: 86-88.
11. McCutcheon L (1997) Taking a bite out of shark cartilage. *Skept Inq* 21:44-48
12. Couzin J (1998) Beefed-up NIH center probes unconventional therapies. *Science* 282:2175-6
13. Holt S, Barila J (1998) *The power of cartilage*. Kensington Publishing
14. Miller D R, Anderson G T, Stark J J, Granick J L, Richardson D (1998) Phase I/II trial of the safety and efficacy of shark cartilage in the treatment of advanced cancer. *J Clin Oncol* 16:2649-55
15. Fontenele J B, Araujo G B, deAlencar J W, deBarros Viana G S (1997) The analgesic and anti-inflammatory effects of shark cartilage are due to a peptide molecule and are nitric oxide (NO) system dependent. *Biol Pharm Bull* 20:1151-4
16. Sculti L (1994) Arthritis benefits from shark cartilage therapy. *Alter Compl Ther* 35-7
17. Gomes E M, Souto P R F, Felzenswalb I (1996) Shark cartilage containing preparation protects cells against hydrogen peroxide induced damage and mutagenesis. *Mut Res* 367:203-8
18. Dupont E, Brazeau P, Juneau C, Maes D H, Marenus K (2000) Methods of using extracts of shark cartilage. U.S. Pat. No. 6,028,118
19. Fontenele J B, Viana G S S, Xavier-Filho J. deAlencar J W, (1996) Antiinflammatory and analgesia activity of a water-soluble fraction from shark cartilage. *Braz J Med Biol Res* 29: 643-6
20. Raithaus L R (1997) Shark liver for stimulating the immune system. U.S. Pat. No. 5,840,342
21. Rosen J, Sherman W T, Prudden J F, Thorbecke G J (1988) Immunoregulatory effects of Catrix. *J Biol Resp Modifiers* 7:498:512
22. Pettit G R, Ode R H (1977) Antineoplastic agents L: Isolation and characterization of sphyrnastatins 1 and 2 from hammerhead shark *Sphyrna lewini*. *J Pharm Sci* 757-9
23. Oikawa T, Ashino-Fuse H, Shimamura M, Koide U, Iwaguchi T (1990) A novel angiogenic inhibitor derived from Japanese shark cartilage (1). *Cancer Lett* 51:181-6
24. Suzuki F, Takigawa M, Hiraki Y, Kato Y, Fukuo K, Shiio T, Yugari Y (1984) Cartilage derived antitumor factor (CATF): A high molecular weight fraction in cartilage extract inhibits solid tumor growth. *J Bone Mineral Metabol* 2:3-7
25. Schinitzky M (1984) Anti-inflamatory composition. U.S. Pat. No. 4,473,551
26. Putney S D, Burke P A (1998) Improving protein therapeutics with sustained-release formulations. *Nature Biotechnol* 16:153-157
27. Cho N-H, Seong S-Y, Chun K-H, Kim Y-H, Kwon I-C, Ahn B-Y, Jeomg S-Y (1998) Novel mucosal immunization with polysaccharide-protein conjugates entrapped in alginate microspheres. *J Control Release* (April 30) 53(1-3): 215-24

28. Moyad M A (2001) Results and lessons from clinical trials using dietary supplements for cancer: direct and indirect investigations. *Semin Urol Oncol* 19:232-46
29. Shepherd F A (2001) Angiogenesis inhibitors in the treatment of lung cancer. *Lung Cancer* 34 Suppl 3:81-9
30. Gonzalez R P, Leyva A, Moraes M O (2001) Shark cartilage as source of antiangiogenic compounds: from basic to clinical research. *Biol Pharm Bull* 24(10):1097-101
31. Codere M G M, Micca P L, Lombardo D T, Hopewell J W (2000) Boron neutron capture therapy of the rat 9L gliosarcoma:evaluation of the effects of shark cartilage. *Brit J Radiol* 73:429-34
32. Hascall V C, Kimura J H (1982) Proteoglycans: Isolation and characterization. *In Methods of Enzymology Vol.* 82 (Cunningham L W, Frederiksen D W, eds.), Academic Press, NY, pp. 769-800
33. Kasai N, Kato K, Takita H, Katsura N (1986) Delayed-type hypersensitivity induced by bovine nasal cartilage proteoglycan in guinea pigs. *Connect Tissue Res* 14:221-8
34. Stocker G, Drzenek Z, Just U, Ostertag W, Sieberts B, Greiling H, Haubeck H-D (1996) Proteoglycan synthesis in human and murine haematopoietic progenitor cell lines: Isolation and characterization of a heparan sulfate proteoglycan as a major proteoglycan from the human haematopoietic cell line TF-1. *Biochem J* 317:203-212
35. Smith P K, Krohn R L, Hermanson G T, Mallia A K, Gartner F H, Provenzano M D, Fujimoto E K, Goeke M N, Olson B J Klenk D C (1985) Measurement of protein using bicinchoninic acid. *Anal Biochem* 150:76-85.
36. Blumenkrantz N, Asboe-Hansen G (1973) New method for quantitative determination of uronic acids. *Anal Biochem* 54:484-9
37. Reissig J L, Strominger J L, Leloir L F (1955) A modified colorimetric method for the estimation of N-acetylamino sugars. *J Biol Chem* 212:959-966
38. Farndale R W, Buttle D J, Barrett A J (1986) Improved quantitation and discrimination of sulphated glycosaminoglycans by use of dimethylmethylene blue. *Biochim Biophys Acta* 883:173-7
39. Wong K F, Middleton N, Montgomery M, Dey M, Carr R I (1988) Immunostimulation by bovine milk protein fractions. *J. Dairy Sci* 81:1825-1832
40. Federko N S (1998) Isolation and purification of proteoglycans. In *Proteoglycans* (Joliet P ed.), Birkhauser, Basel, pp 9-35
41. Chandrasekhar S, Esterman M A, Hoffman H A (1987) Microdetermination of proteoglycans and glcosaminoglycans in the presence of guanidine hydrochloride. *Anal Biochem* 61:103-8
42. Sweet M J, Hume, D A (1996) Endotoxin signal transduction in macrophages. *J Leukoc Biol* 60:8-26
43. Lynn W A, Golenbock D T (1992) Lipopolysaccharide antagonists. *Immunol Today* 13:271-276
44. Danner R L, Joiner K A, Rubin M, Patterson W H, Johnson N, Ayers K M, Parillo J E (1989) Purification, toxicity, and anti-endotoxin activity of polymyxin B nonapeptide. *Antimicrob Agents Chemother* 33:1428-1434
45. Sultzer B M, Castagna R, Bandekar J, Wong P (1993) Lipopolysaccharide nonresponder cells: the C3H/HeJ defect. *Immunobiology* 187:257-352
46. Kishikawa H, Song R, Lawrence D A. (1997) Interleukin-12 promotes enhanced resistance to *Listeria monocytogenes* infection of lead-exposed mice. *Toxicol Appl Pharmacol* 147:180-189
47. Li X Y, Takamoto H, Miura S, Yoshikai Y, Matsuzaki G, Momoto K (1992) Effect of a traditional Chinese medicine, bu-zhong-yl-qi-tang (Japanese name: Hochu-ekki-to) on the protection against *Listeria monocytogenes* infection in mice. *Immunopharmacol Immunotoxicol* 1992; 14(3):383-402
48. Hascall V C, Calabro A, Midura R J, Yanagishita M (1992) Isolation and characterization of proteoglycans. In *Methods of Enzymology Vol.* 230 (Lennarz W J, Hart G W eds.) Academic Press, NY, pp. 390-417
49. Morel P A, Criss T B (1998) Cross-regulation between Th1 or Th2 cells. *Crit Rev Immunol* 18: 275-303

The invention claimed is:

1. A method for inhibiting proliferation of *Listeria* in a subject, said method comprising orally administering to a subject having a *Listeria* infection a composition from shark cartilage in an amount sufficient to inhibit proliferation of said *Listeria*, said composition comprising proteoglycans having a molecular weight greater than about 100 KD, said composition having a uronic acid content of about 0.05-0.5 µg glucuronic acid per µg of the composition.

2. The method according to claim 1, wherein said *Listeria* is *Listeria monocytogenes*.

3. The method according to claim 1, wherein said proteoglycans have an average molecular weight of about 500 KD.

4. The method according to claim 1, wherein said proteoglycans have a molecular weight greater than about 1 MD.

5. The method according to claim 1, wherein the uronic acid content of said composition is about 0.08-0.3 µg glucuronic acid per µg of the composition.

6. The method according to claim 1, wherein said composition comprises xylose, rhamnose, galactose, glucose or mixtures thereof.

7. The method according to claim 1, wherein said composition comprises aminosugars.

8. The method according to claim 1, wherein said composition comprises about 20-30% protein by weight of said composition.

9. The method according to claim 1, wherein the glycine content of said composition is about 14-16% by weight of total amino acids, the proline content of said composition is about 14-15% by weight of total amino acids, the alanine content of said composition is about 12-14% by weight of total amino acids, the glutamic acid content of said composition is about 10-12% by weight of total amino acids, the aspartic acid content of said composition is about 6-7% by weight of total amino acids, and the arginine content of said composition is about 5-7% by weight of total amino acids.

10. The method according to claim 1, wherein said composition comprises a physiologically acceptable carrier, excipient and/or diluent.

11. The method according to claim 1, wherein said proteoglycans have a molecular weight greater than about 500 KD.

12. The method according to claim 1, comprising the further step of, prior to said administering step, diagnosing a *Listeria* infection in said subject.

* * * * *